(12) United States Patent
Stuer-Lauridsen et al.

(10) Patent No.: US 8,137,950 B2
(45) Date of Patent: Mar. 20, 2012

(54) BACTERIOPHAGE RESISTANT LACTIC ACID BACTERIA

(75) Inventors: Birgitte Stuer-Lauridsen, Virum (DK); Thomas Janzen, Frederiksberg (DK)

(73) Assignee: Chr. Hansen A/S, Horsholm (DK)

( * ) Notice: Subject to any disclaimer, the term of this patent is extended or adjusted under 35 U.S.C. 154(b) by 798 days.

(21) Appl. No.: 11/794,862

(22) PCT Filed: Jan. 6, 2006

(86) PCT No.: PCT/EP2006/050078
§ 371 (c)(1),
(2), (4) Date: Jan. 17, 2008

(87) PCT Pub. No.: WO2006/072631
PCT Pub. Date: Jul. 13, 2006

(65) Prior Publication Data
US 2008/0317903 A1  Dec. 25, 2008

Related U.S. Application Data

(60) Provisional application No. 60/643,591, filed on Jan. 14, 2005.

(30) Foreign Application Priority Data

Jan. 6, 2005 (EP) .................... 05100052

(51) Int. Cl.
  C12N 1/20   (2006.01)
  C12N 15/00  (2006.01)
  C12N 9/00   (2006.01)
  C12Q 1/00   (2006.01)
  C07H 21/04  (2006.01)
  C07H 21/02  (2006.01)

(52) U.S. Cl. ............ 435/252.3; 435/440; 435/183; 435/252.9; 435/4; 435/320.1; 536/23.2; 536/23.1

(58) Field of Classification Search .................... None
See application file for complete search history.

(56) References Cited

FOREIGN PATENT DOCUMENTS

WO  01/77334  10/2001

OTHER PUBLICATIONS

Branden et al. Introduction to Protein Structure, Garland Publishing Inc., New York, p. 247, 1991.*
International Search Report for PCT/EP2006/050078 mailed Mar. 28, 2006.
Written Opinion for PCT/EP2006/050078 mailed Mar. 28, 2006 (5 pages).
Bolotin et al., "The Complete Genome Sequence of the Lactic Acid Bacterium *Lactococcus lactis* ssp. Lactis IL1403," Genome Research, vol. 11, No. 5, May 2001, pp. 731-753, XP001109416 and Database EMBL [Online], Feb. 10, 2001, "*Lactococcus lactis* subsp. lactis IL1043 section 84 of 218 of the complete genome," XP002371848, retrieved from EBI accession No. EM_PRO:AE006322, Database accession No. AE006322 and Database UniProt [Online], Jun. 1, 2001, "Hypothetical protein yjaE," XP002329279, retrieved from EBI accession No. UNIPROT:Q9CH57, database accession No. Q9CH57.
Kraus et al., "Membrane receptor for prolate phages is not required for infection of *Lactococcus lactis* by small or large isometric phages," Journal of Dairy Science, vol. 81, No. 9, Sep. 1998, pp. 2329-2335, XP002371844.
Dupont et al., "Identification of *Lactococcus lactis* genes required for bacteriophage adsorption," Applied and Environmental Microbiology, vol. 70, No. 10, Oct. 2004, pp. 5825-5832, XP002371845.
Madera et al., "Characterisation of technologically proficient wild *Lactococcus lactis* strains resistant to phage infection," International Journal of Food Microbiology, vol. 86, No. 3, Sep. 15, 2003, pp. 213-222, XP002371846.
Kraus and Geller, "Membrane Receptor for Prolate Phages is Not Required for Infection of *Lactococcus lactis* by Small or Large Isometric Phages", J. Dairy Sci. 81:2329-2335 (1998).
Bolotin et al, "The Complete Genome Sequence of the Lactic Acid Bacterium *Lactococcus lactis* ssp. lactis IL1403", Genome Research 11(5):731-753 (2001)—XP001109416 & Database EMBL [Online] Feb. 10, 2001, "*Lactococcus lactis* subsp. lactis IL1403 section 84 of 218 of the complete genome"—XP002371848 retrieved from EBI accession No. EM_PRO:AE006322 & Database UniProt [Online] Jun. 1, 2001, "Hypothetical protein yjaE"—XP002329279.
Valyasevi et al, "A Membrane Protein Is Required for Bacteriophage c2 Infection of *Lactococcus lactis* subsp. lactis C2", Journal of Bacteriology 173(19):6095-6100 (1991).
Silveira et al, "Effect of Adaptation to Ethanol on Cytoplasmic and Membrane Protein Profiles of *Oenococcus oeni*", Applied and Environmental Microbiology 70(5):2748-2755 (2004).
Nouwens et al, "Complementing genomics with proteomics: The membrane subproteome of *Pseudomonas aeruginosa* PAO1", Electrophoresis 21:3797-3809 (2000).
Molloy et al, "Proteomic analysis of the *Escherichia coli* outer membrane", Eur. J. Biochem. 267:2871-2881 (2000).
Hill, "Bacteriophage and bacteriophage resistance in lactic acid bacteria", FEMS Microbiology Reviews 12:87-108 (1993).
Dinsmore and Klaenhammer, "Bacteriophage Resistance in *Lactococcus*", Molecular Biotechnology 4(3):297-314 (1995).
Allison and Klaenhammer, "Phage Resistance Mechanisms in Lactic Acid Bacteria", Int. Dairy Journal 8(3):207-226 (1998).
Dupont et al, "identification of *Lactococcus lactis* Genes Required for Bacteriophage Adsorption", Applied and Environmental Microbiology 70(10):5825-5832 (2004).
Madera et al, "Characterisation of technologically proficient wild *Lactococcus lactis* strains resistant to phage infection", Int. Journal of Food Microbiology 86:213-222 (2003).

* cited by examiner

*Primary Examiner* — Yong Pak
(74) *Attorney, Agent, or Firm* — Nixon & Vanderhye P.C.

(57) ABSTRACT

A lactic acid bacterium (LAB) wherein an YjaE protein is essentially inactive and the LAB thereby get improved resistance to bacteriophages, a starter culture composition comprising the lactic acid bacterium and use of this starter culture manufacturing a food or feed product.

20 Claims, 1 Drawing Sheet

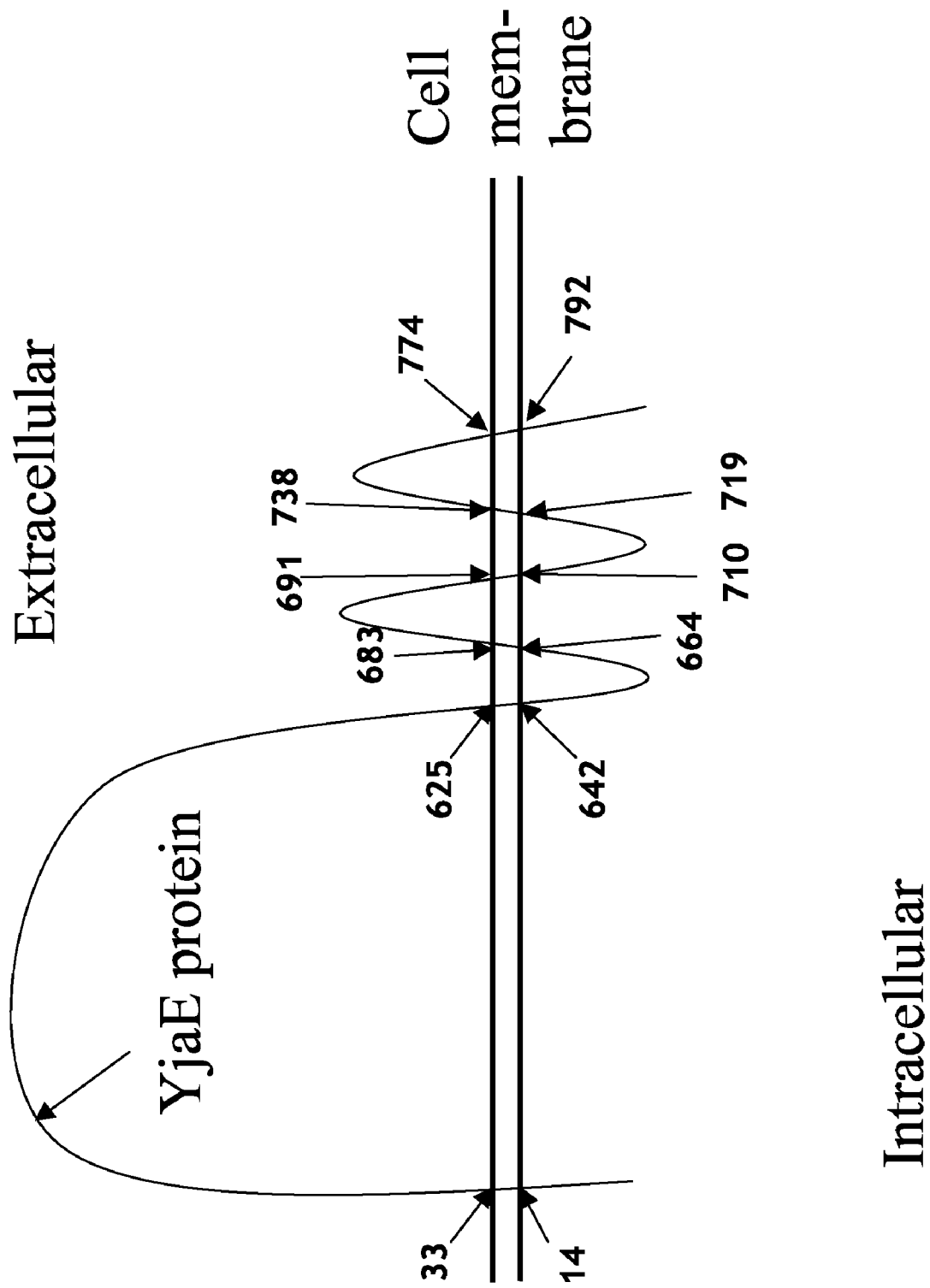

SEQUENCE LISTING

```
<160> NUMBER OF SEQ ID NOS: 2

<210> SEQ ID NO 1
<211> LENGTH: 2400
<212> TYPE: DNA
<213> ORGANISM: Lactococcus lactis
<220> FEATURE:
<221> NAME/KEY: CDS
<222> LOCATION: (1)..(2400)
<223> OTHER INFORMATION:

<400> SEQUENCE: 1 atg tta aaa aaa gaa tgg caa gcc att tta aag cac aaa ttt ttt att      48
Met Leu Lys Lys Glu Trp Gln Ala Ile Leu Lys His Lys Phe Phe Ile
1               5                   10                  15 att gtt att atc gct ttg gca ctt gta cca gca att tat aac tat att      96
Ile Val Ile Ile Ala Leu Ala Leu Val Pro Ala Ile Tyr Asn Tyr Ile
            20                  25                  30 ttc tta ggt tct atg tgg gat cct tac ggt aaa ttg aat gac tta cca     144
Phe Leu Gly Ser Met Trp Asp Pro Tyr Gly Lys Leu Asn Asp Leu Pro
        35                  40                  45 gta gcg gtt gta aat tta gac aag acg tct gaa ttg aac gga aaa aaa     192
Val Ala Val Val Asn Leu Asp Lys Thr Ser Glu Leu Asn Gly Lys Lys
    50                  55                  60 ttc aaa ctt ggt gat gat gtc att gct gaa atg aaa aaa tca aag gat     240
Phe Lys Leu Gly Asp Asp Val Ile Ala Glu Met Lys Lys Ser Lys Asp
65                  70                  75                  80 tta gat tat cat ttt gtt tcg gag tat aaa gct tct aaa ggg ata aaa     288
Leu Asp Tyr His Phe Val Ser Glu Tyr Lys Ala Ser Lys Gly Ile Lys
                85                  90                  95
```

```
aaa ggt gat tat tac atg gtt atc act ttt cca gaa aac ttt tca gaa    336
Lys Gly Asp Tyr Tyr Met Val Ile Thr Phe Pro Glu Asn Phe Ser Glu
        100                 105                 110 aat gca aca acc tta atg aat aag aaa cca aaa acg gtt cag tta gat    384
Asn Ala Thr Thr Leu Met Asn Lys Lys Pro Lys Thr Val Gln Leu Asp
            115                 120                 125 tat caa acg aca cgt ggt cat aac tat att tca tca aaa atg agc gaa    432
Tyr Gln Thr Thr Arg Gly His Asn Tyr Ile Ser Ser Lys Met Ser Glu
        130                 135                 140 agt gcg atg aat cag ctg aaa tca gag gtt tct aaa aat atc acg gaa    480
Ser Ala Met Asn Gln Leu Lys Ser Glu Val Ser Lys Asn Ile Thr Glu
145                 150                 155                 160 act tac acc aaa gaa att ttc gct aaa ctt ggt gat atg aag tca gga    528
Thr Tyr Thr Lys Glu Ile Phe Ala Lys Leu Gly Asp Met Lys Ser Gly
                165                 170                 175 atg aaa gaa gct tct gac ggt tca aat aaa ttg gct gat gga act tcg    576
Met Lys Glu Ala Ser Asp Gly Ser Asn Lys Leu Ala Asp Gly Thr Ser
            180                 185                 190 tca gca tta aat ggt tca aaa gaa tta agt agt aat ttg aat act tta    624
Ser Ala Leu Asn Gly Ser Lys Glu Leu Ser Ser Asn Leu Asn Thr Leu
        195                 200                 205 tct tca tca agt tta act ttt act gac ggc gca aat aat ttg aat tca    672
Ser Ser Ser Ser Leu Thr Phe Thr Asp Gly Ala Asn Asn Leu Asn Ser
210                 215                 220 ggc tta aat aaa tat gta tca gga gtg aat caa gct gcc aat ggg gga    720
Gly Leu Asn Lys Tyr Val Ser Gly Val Asn Gln Ala Ala Asn Gly Gly
225                 230                 235                 240 caa caa ctt tct tct ggt gca gac caa ttt gtc agt gga acg caa caa    768
Gln Gln Leu Ser Ser Gly Ala Asp Gln Phe Val Ser Gly Thr Gln Gln
                245                 250                 255 tta gca gca ggt aca caa aca ctg gct gat aaa tca aaa gag ctg tca    816
Leu Ala Ala Gly Thr Gln Thr Leu Ala Asp Lys Ser Lys Glu Leu Ser
            260                 265                 270 gca gga att tca caa att tct caa ggg tca gaa gcg gtg agt caa ttg    864
Ala Gly Ile Ser Gln Ile Ser Gln Gly Ser Glu Ala Val Ser Gln Leu
        275                 280                 285 caa tcg ggt gtg caa caa tta tct gaa ggc tta agt caa atg gct caa    912
Gln Ser Gly Val Gln Gln Leu Ser Glu Gly Leu Ser Gln Met Ala Gln
290                 295                 300 aaa aca act tta tcc gaa act caa cag caa aat att agt gct gta caa    960
Lys Thr Thr Leu Ser Glu Thr Gln Gln Gln Asn Ile Ser Ala Val Gln
305                 310                 315                 320 aat ggt ctt act gaa tta aat cag gag tta caa aaa aat acg att gac   1008
Asn Gly Leu Thr Glu Leu Asn Gln Glu Leu Gln Lys Asn Thr Ile Asp
                325                 330                 335 cca aat ttg gct gcc aat atc caa aat aac ttg aaa ggt ctt gga gct   1056
Pro Asn Leu Ala Ala Asn Ile Gln Asn Asn Leu Lys Gly Leu Gly Ala
            340                 345                 350 acg gtc aca aat cta gct aat gat caa gtg gcg gcc tct aag aca gca   1104
Thr Val Thr Asn Leu Ala Asn Asp Gln Val Ala Ala Ser Lys Thr Ala
        355                 360                 365 gtt gaa agt act gag act ttt aaa act tta agc gaa agt cag aaa aca   1152
Val Glu Ser Thr Glu Thr Phe Lys Thr Leu Ser Glu Ser Gln Lys Thr
370                 375                 380 gat ata aga aat gca tta gat aat tct gtt ggt gct gga gca gtt caa   1200
Asp Ile Arg Asn Ala Leu Asp Asn Ser Val Gly Ala Gly Ala Val Gln
385                 390                 395                 400 acc gat tta cta tct tta aat aag aat att aaa gga gtc caa gac agt   1248
Thr Asp Leu Leu Ser Leu Asn Lys Asn Ile Lys Gly Val Gln Asp Ser
                405                 410                 415
```

-continued

| | | |
|---|---|---|
| ctt aca agt cta cta cca atg ttt gga aaa att gct gat ctt aaa aca<br>Leu Thr Ser Leu Leu Pro Met Phe Gly Lys Ile Ala Asp Leu Lys Thr<br>420 425 430 | | 1296 |
| tta gtt cca gga gca agt caa ata att gct gac ctt tca ggt ggt ctg<br>Leu Val Pro Gly Ala Ser Gln Ile Ile Ala Asp Leu Ser Gly Gly Leu<br>435 440 445 | | 1344 |
| aac gaa gta aac act aat gta aac aca aaa ttt att cct ggt atc aat<br>Asn Glu Val Asn Thr Asn Val Asn Thr Lys Phe Ile Pro Gly Ile Asn<br>450 455 460 | | 1392 |
| cag tta aat gct ggt ttg acg aat ttt aat gac cag tta act tct gga<br>Gln Leu Asn Ala Gly Leu Thr Asn Phe Asn Asp Gln Leu Thr Ser Gly<br>465 470 475 480 | | 1440 |
| agt caa aaa tta act tct ggt ttt gcc caa tat gct gac gga gtt aat<br>Ser Gln Lys Leu Thr Ser Gly Phe Ala Gln Tyr Ala Asp Gly Val Asn<br>485 490 495 | | 1488 |
| caa gca aac gct ggc gct caa caa tta gca agt aaa tca aaa gat tta<br>Gln Ala Asn Ala Gly Ala Gln Gln Leu Ala Ser Lys Ser Lys Asp Leu<br>500 505 510 | | 1536 |
| caa agc ggg aca atg caa tta gtt tct gga ttg tca caa tta caa gcg<br>Gln Ser Gly Thr Met Gln Leu Val Ser Gly Leu Ser Gln Leu Gln Ala<br>515 520 525 | | 1584 |
| aat ggt tca act tta act tca ggt tca aat caa ttg gca ggg ggt gct<br>Asn Gly Ser Thr Leu Thr Ser Gly Ser Asn Gln Leu Ala Gly Gly Ala<br>530 535 540 | | 1632 |
| caa caa att tcc tct gtt tca caa caa ttg gca aat gga ggt tca agt<br>Gln Gln Ile Ser Ser Val Ser Gln Gln Leu Ala Asn Gly Gly Ser Ser<br>545 550 555 560 | | 1680 |
| tta aca agt ggt ttg gga acg cta aat aca ggg gct aat aac ttg tca<br>Leu Thr Ser Gly Leu Gly Thr Leu Asn Thr Gly Ala Asn Asn Leu Ser<br>565 570 575 | | 1728 |
| aca gcg tta acc aaa gca gat gat act ctc tca gca act aat aat tct<br>Thr Ala Leu Thr Lys Ala Asp Asp Thr Leu Ser Ala Thr Asn Asn Ser<br>580 585 590 | | 1776 |
| aat gaa aat gct aaa aaa gta gct gca ccg ttg aaa ctt aaa cat act<br>Asn Glu Asn Ala Lys Lys Val Ala Ala Pro Leu Lys Leu Lys His Thr<br>595 600 605 | | 1824 |
| gac cat gac aat gta cca gaa aat ggt gca gga atg aca cca tac atg<br>Asp His Asp Asn Val Pro Glu Asn Gly Ala Gly Met Thr Pro Tyr Met<br>610 615 620 | | 1872 |
| att aat gtt gct ctc ttt att ggt gcc ctt gcg aca aat gtt gtg att<br>Ile Asn Val Ala Leu Phe Ile Gly Ala Leu Ala Thr Asn Val Val Ile<br>625 630 635 640 | | 1920 |
| gga att ggt ttc tca ggt gaa aaa tgg aaa tct ggt cgc gaa ttt atg<br>Gly Ile Gly Phe Ser Gly Glu Lys Trp Lys Ser Gly Arg Glu Phe Met<br>645 650 655 | | 1968 |
| ttg gcg aaa att ggt aca aat ggt ttg gta gca ctt tta caa gga atc<br>Leu Ala Lys Ile Gly Thr Asn Gly Leu Val Ala Leu Leu Gln Gly Ile<br>660 665 670 | | 2016 |
| atc gtc tgg gga gca gtt gct ctt ctt gga ttg aga cca aat cat ttg<br>Ile Val Trp Gly Ala Val Ala Leu Leu Gly Leu Arg Pro Asn His Leu<br>675 680 685 | | 2064 |
| tgg gaa atg ttg ttg tca gta ctt tta atc agc ttc gct tac atg gca<br>Trp Glu Met Leu Leu Ser Val Leu Leu Ile Ser Phe Ala Tyr Met Ala<br>690 695 700 | | 2112 |
| atc aat act ttc ttc tta acg gct cta ggt aag att ggt gaa ttc ctt<br>Ile Asn Thr Phe Phe Leu Thr Ala Leu Gly Lys Ile Gly Glu Phe Leu<br>705 710 715 720 | | 2160 |
| atg att gtt gtc tta gtt cta caa ctg gcg acg agt gca gga act tac<br>Met Ile Val Val Leu Val Leu Gln Leu Ala Thr Ser Ala Gly Thr Tyr<br>725 730 735 | | 2208 |

```
ccc tta caa ctt gcg cct aaa ata tat caa gtc atc agt cct tgg tta      2256
Pro Leu Gln Leu Ala Pro Lys Ile Tyr Gln Val Ile Ser Pro Trp Leu
            740                 745                 750 cca atg act tat ggt tta aaa atg tta cgc gaa acc att ggt ttg aat      2304
Pro Met Thr Tyr Gly Leu Lys Met Leu Arg Glu Thr Ile Gly Leu Asn
        755                 760                 765 gga gca att tta cca gaa gca atc cta ttt gta gtt att atc gct ctc      2352
Gly Ala Ile Leu Pro Glu Ala Ile Leu Phe Val Val Ile Ile Ala Leu
    770                 775                 780 ttt act ttc atg ttg agt ttc ttc aag aaa ttc tca cgt ttt gca taa      2400
Phe Thr Phe Met Leu Ser Phe Phe Lys Lys Phe Ser Arg Phe Ala
785                 790                 795

<210> SEQ ID NO 2
<211> LENGTH: 799
<212> TYPE: PRT
<213> ORGANISM: Lactococcus lactis

<400> SEQUENCE: 2

Met Leu Lys Lys Glu Trp Gln Ala Ile Leu Lys His Lys Phe Phe Ile
1               5                   10                  15

Ile Val Ile Ile Ala Leu Ala Leu Val Pro Ala Ile Tyr Asn Tyr Ile
            20                  25                  30

Phe Leu Gly Ser Met Trp Asp Pro Tyr Gly Lys Leu Asn Asp Leu Pro
        35                  40                  45

Val Ala Val Val Asn Leu Asp Lys Thr Ser Glu Leu Asn Gly Lys Lys
    50                  55                  60

Phe Lys Leu Gly Asp Asp Val Ile Ala Glu Met Lys Lys Ser Lys Asp
65                  70                  75                  80

Leu Asp Tyr His Phe Val Ser Glu Tyr Lys Ala Ser Lys Gly Ile Lys
                85                  90                  95

Lys Gly Asp Tyr Tyr Met Val Ile Thr Phe Pro Glu Asn Phe Ser Glu
            100                 105                 110

Asn Ala Thr Thr Leu Met Asn Lys Lys Pro Lys Thr Val Gln Leu Asp
        115                 120                 125

Tyr Gln Thr Thr Arg Gly His Asn Tyr Ile Ser Ser Lys Met Ser Glu
    130                 135                 140

Ser Ala Met Asn Gln Leu Lys Ser Glu Val Ser Lys Asn Ile Thr Glu
145                 150                 155                 160

Thr Tyr Thr Lys Glu Ile Phe Ala Lys Leu Gly Asp Met Lys Ser Gly
                165                 170                 175

Met Lys Glu Ala Ser Asp Gly Ser Asn Lys Leu Ala Asp Gly Thr Ser
            180                 185                 190

Ser Ala Leu Asn Gly Ser Lys Glu Leu Ser Ser Asn Leu Asn Thr Leu
        195                 200                 205

Ser Ser Ser Ser Leu Thr Phe Thr Asp Gly Ala Asn Asn Leu Asn Ser
    210                 215                 220

Gly Leu Asn Lys Tyr Val Ser Gly Val Asn Gln Ala Ala Asn Gly Gly
225                 230                 235                 240

Gln Gln Leu Ser Ser Gly Ala Asp Gln Phe Val Ser Gly Thr Gln Gln
                245                 250                 255

Leu Ala Ala Gly Thr Gln Thr Leu Ala Asp Lys Ser Lys Glu Leu Ser
            260                 265                 270

Ala Gly Ile Ser Gln Ile Ser Gln Gly Ser Glu Ala Val Ser Gln Leu
        275                 280                 285

Gln Ser Gly Val Gln Gln Leu Ser Glu Gly Leu Ser Gln Met Ala Gln
    290                 295                 300
```

```
Lys Thr Thr Leu Ser Glu Thr Gln Gln Asn Ile Ser Ala Val Gln
305                 310                 315                 320

Asn Gly Leu Thr Glu Leu Asn Gln Glu Leu Gln Lys Asn Thr Ile Asp
            325                 330                 335

Pro Asn Leu Ala Ala Asn Ile Gln Asn Asn Leu Lys Gly Leu Gly Ala
                340                 345                 350

Thr Val Thr Asn Leu Ala Asn Asp Gln Val Ala Ala Ser Lys Thr Ala
            355                 360                 365

Val Glu Ser Thr Glu Thr Phe Lys Thr Leu Ser Glu Ser Gln Lys Thr
        370                 375                 380

Asp Ile Arg Asn Ala Leu Asp Asn Ser Val Gly Ala Gly Ala Val Gln
385                 390                 395                 400

Thr Asp Leu Leu Ser Leu Asn Lys Asn Ile Lys Gly Val Gln Asp Ser
                405                 410                 415

Leu Thr Ser Leu Leu Pro Met Phe Gly Lys Ile Ala Asp Leu Lys Thr
            420                 425                 430

Leu Val Pro Gly Ala Ser Gln Ile Ile Ala Asp Leu Ser Gly Gly Leu
        435                 440                 445

Asn Glu Val Asn Thr Asn Val Asn Thr Lys Phe Ile Pro Gly Ile Asn
450                 455                 460

Gln Leu Asn Ala Gly Leu Thr Asn Phe Asn Asp Gln Leu Thr Ser Gly
465                 470                 475                 480

Ser Gln Lys Leu Thr Ser Gly Phe Ala Gln Tyr Ala Asp Gly Val Asn
            485                 490                 495

Gln Ala Asn Ala Gly Ala Gln Leu Ala Ser Lys Ser Lys Asp Leu
        500                 505                 510

Gln Ser Gly Thr Met Gln Leu Val Ser Gly Leu Ser Gln Leu Gln Ala
    515                 520                 525

Asn Gly Ser Thr Leu Thr Ser Gly Ser Asn Gln Leu Ala Gly Gly Ala
    530                 535                 540

Gln Gln Ile Ser Ser Val Ser Gln Gln Leu Ala Asn Gly Gly Ser Ser
545                 550                 555                 560

Leu Thr Ser Gly Leu Gly Thr Leu Asn Thr Gly Ala Asn Asn Leu Ser
            565                 570                 575

Thr Ala Leu Thr Lys Ala Asp Asp Thr Leu Ser Ala Thr Asn Asn Ser
            580                 585                 590

Asn Glu Asn Ala Lys Lys Val Ala Ala Pro Leu Lys Leu Lys His Thr
        595                 600                 605

Asp His Asp Asn Val Pro Glu Asn Gly Ala Gly Met Thr Pro Tyr Met
    610                 615                 620

Ile Asn Val Ala Leu Phe Ile Gly Ala Leu Ala Thr Asn Val Val Ile
625                 630                 635                 640

Gly Ile Gly Phe Ser Gly Glu Lys Trp Lys Ser Gly Arg Glu Phe Met
            645                 650                 655

Leu Ala Lys Ile Gly Thr Asn Gly Leu Val Ala Leu Gln Gly Ile
            660                 665                 670

Ile Val Trp Gly Ala Val Ala Leu Leu Gly Leu Arg Pro Asn His Leu
        675                 680                 685

Trp Glu Met Leu Leu Ser Val Leu Leu Ile Ser Phe Ala Tyr Met Ala
    690                 695                 700

Ile Asn Thr Phe Phe Leu Thr Ala Leu Gly Lys Ile Gly Glu Phe Leu
705                 710                 715                 720

Met Ile Val Val Leu Val Leu Gln Leu Ala Thr Ser Ala Gly Thr Tyr
```

-continued

```
                        725                     730                      735
Pro Leu Gln Leu Ala Pro Lys Ile Tyr Gln Val Ile Ser Pro Trp Leu
            740                     745                      750

Pro Met Thr Tyr Gly Leu Lys Met Leu Arg Glu Thr Ile Gly Leu Asn
            755                     760                      765

Gly Ala Ile Leu Pro Glu Ala Ile Leu Phe Val Val Ile Ile Ala Leu
            770                     775                      780

Phe Thr Phe Met Leu Ser Phe Phe Lys Lys Phe Ser Arg Phe Ala
785                     790                      795
```

US 8,137,950 B2

BACTERIOPHAGE RESISTANT LACTIC ACID BACTERIA

This application is the US national phase of international application PCT/EP2006/050078 filed 6 Jan. 2006, which designated the U.S. and claims benefit of EP 05100052.9 filed 6 Jan. 2005, and U.S. Provisional Application No. 60/643,591, filed 14 Jan. 2005, the entire contents of each of which are hereby incorporated by reference.

FIELD OF THE INVENTION

The present invention relates to a lactic acid bacterium (LAB) wherein the YjaE protein is essentially inactive and the LAB thereby get improved resistance to bacteriophages, a starter culture composition comprising the lactic acid bacterium and use of this starter culture manufacturing a food or feed product.

BACKGROUND ART

Production failures of bacterial cultures caused by bacteriophage infection are considered to be one of the major problems in industrial use of bacterial cultures. Bacteriophages have been found for many of the bacterial strains used in the industry, such as species of lactic acid bacteria e.g. *Lactococcus* sp., *Lactobacillus* sp., *Leuconostoc* sp., *Pediococcus* sp. or *Streptococcus* sp.

In the food industry lactic acid bacterial starter cultures are widely used for food fermentations. It appears that among members of the lactic acid bacteria *Lactococcus* sp. are most devastated by bacteriophage infections. A factor, which leads to frequent bacteriophage infections in lactic acid bacterial starter cultures, is the fact that the fermentation conditions in the food industry including the dairy industry are generally non-sterile. Thus, it has not yet been possible to eliminate bacteriophage contamination under these industrial conditions.

The lytic development of bacteriophages involves adsorption of the phages to the host cell surface, injection of phage DNA into the cell, synthesis of phage proteins, replication of phage DNA, assembly of progeny phages and release of progeny from the host. Cell-mediated mechanisms of interference with any of these events can prevent a phage infection. The ability of bacterial cultures to resist bacteriophage infection during industrial use depends to a large extent on host strain characteristics affecting one or more of the above mechanisms.

*Lactococcus lactis* contains a chromosomal gene (pip) for a membrane protein that serves as a receptor for the prolate bacteriophage c2 and other phages of the c2 species. Currently, an industrial preferred method to make bacteriophage resistant *Lactococcus* strains is to make a strain where the pip gene is inactivated.

The article (Kraus J. et al, 1998 J. Dairy Science 81:2339-2335) describes construction of a number of commercially relevant *Lactococcus lactis* strains where the pip gene was inactivated (pip⁻ strains). The pip⁻ strains were completely resistant to prolate bacteriophage of the c2 species but were fully sensitive to small isometric phage sk1 of the 936 species, small isometric phages mm210b and 31 (p335 species) and to the large isometric phage 949 (949 species).

The complete genome of the *Lactococcus lactis* IL1403 strain has been sequenced and is published in the Genbank database.

yjaE is a gene of the *Lactococcus lactis* IL1403 strain.

On the filing date of the present invention Genbank Accession no.: AE006322 showed section 84 of the 218 sections of the complete genome of *Lactococcus lactis* subsp. *lactis* IL1403. The coding DNA sequence of the yjaE gene was given as CDS sequence from 5892 to 8291. With respect to function was simply said "Hypothetical protein". It was also said that the yjaE gene has a low homology to the pip gene. More specifically it was said "22% identical to phage infection protein pip."

Genbank Accession no.: NC_002662 showed the complete sequence of *Lactococcus lactis* subsp. *lactis* IL1403. Here the coding DNA sequence of the yjaE gene was given as CDS sequence from 904024 to 906423.

WO01/77334 discloses the complete genome sequence of *Lactococcus lactis* subsp. *lactis* IL1403. In this document the yjaE gene corresponds to ORF 900. No function is attributed to this ORF 900. On pages 27-29 are described several genes that are involved in the bacterio-phage resistance. Page 29, lines 2-3 summarizes these bacteriophage related genes as ORF 38, 41, 448, 452, 518, 1461 and 1472.

In summary, from a technical point of view the function of the yjaE gene was unknown at the filing date of the present application.

SUMMARY OF THE INVENTION

The problem to be solved by the present invention is to provide a novel lactic acid bacterium (LAB), which is resistant to bacteriophages.

The solution is based on that the present inventors have identified that the yjaE gene is involved in this. The present inventors inactivated the yjaE gene in different *Lactococcus lactis* bacterial strains and found that these yjaE strains were resistant to bacteriophages. See working examples herein.

As explained above the DNA sequence of the yjaE gene of *Lactococcus lactis* subsp. *lactis* IL1403 strain is published in Genbank. The coding DNA sequence is shown in SEQ ID NO 1 herein and the corresponding amino acid sequence of the yjaE protein is shown in SEQ ID NO 2 herein.

Accordingly, a first aspect of the invention relates to a lactic acid bacterium wherein an YjaE protein, expressed by an yjaE gene, is essentially inactive and wherein the YjaE protein is expressed by a yjaE gene comprising a DNA sequence selected from the group consisting of:

(a) the DNA sequence shown in positions 1-2400 in SEQ ID NO 1 (IL1403 yjaE DNA coding sequence);

(b) a DNA sequence that encodes a polypeptide, optionally having YjaE protein activity, that is at least 70% such as at least 80%, preferably at least 90%, e.g. at least 95% or even at least 99% identical to the polypeptide sequence shown in positions 1-799 of SEQ ID NO 2 (IL1403 YjaE protein sequence).

The term "essentially inactive" should be understood in relation to the objective of the present invention. The objective is to make a strain where the YjaE protein works substantially worse than in a corresponding parent wild-type strain. As explained below it is routine work for the skilled person to make such a strain. For instance by introducing a stop codon or a frame shift insertion in the yjaE gene, which could give a non-functional gene that would e.g. either express no YjaE protein or express a partial length inactive YjaE protein. Alternatively, a mutation could be made in the gene, which e.g. could give an YjaE protein mutation variant that has some activity but which for all herein related practical objectives is essentially inactive. A way to measure the inactivity of the YjaE protein is simply to analyze the bacterium for increased resistance to a suitable representative panel of different bacteriophages. As explained below this is routine work for the skilled person and if the bacterium as described herein has a substantial increased resistance to the panel of bacteriophages then it is herein understood that the YjaE protein is essentially inactive. As explained above, it is known that a lactic acid bacterium may be sensitive to some bacteriophage but not to others. Accordingly, as would be understood in the art, when herein is said that the bacterium has increased resistance to a suitable representative panel of different bacteriophages it is meant that it has improved resistance to at least one of the bacteriophages of panel. Of course, it is generally preferred that the bacterium has improved resistance to two or more bacteriophages of panel.

An advantage of essentially inactivating the YjaE protein is that one may get a bacterium that is not only resistant towards c2 type bacteriophages but also to other types of bacteriophages. See working examples herein wherein it is demonstrated that a LAB as described herein is resistant towards prolate bacteriophages of the c2 species and also resistant towards small isometric phages of the 936 species.

This is an improvement over pip⁻ strains, which as described above generally only are resistant to bacteriophages of the c2 species.

Further to essentially inactivate the YjaE protein does generally not negatively affect viability, growth rate or acid production of the LAB. See working examples herein where this is demonstrated for two different strains.

A second aspect of the invention relates to a starter culture composition comprising the lactic acid bacterium of the first aspect.

A third aspect of the invention relates to a method of manufacturing a food or feed product comprising adding a starter culture composition according to the second aspect to a food or feed product starting material and keeping the thus inoculated starting material under conditions where the lactic acid bacterium is metabolically active.

A fourth aspect of the invention relates to a method for making a lactic acid bacterium wherein the YjaE protein, expressed by the yjaE gene, is essentially inactive comprising making a suitable modification of the yjaE gene in order not to get expression of an active YjaE protein, wherein the yjaE gene comprises a DNA sequence selected from the group consisting of:
  (a) the DNA sequence shown in positions 1-2400 in SEQ ID NO 1 (IL1403 yjaE DNA coding sequence);
  (b) a DNA sequence that encodes a polypeptide, optionally having YjaE protein activity, that is at least 80% such as at least 85%, preferably at least 90%, e.g. at least 95% or even at least 99% identical to the polypeptide sequence shown in positions 1-799 of SEQ ID NO 2 (IL1403 YjaE protein sequence).

Embodiment of the present invention is described below, by way of examples only.

DETAILED DESCRIPTION OF THE INVENTION

According to invention the solution to the problem of providing novel lactic acid bacteria (LAB), which are resistant to bacteriophages is to provide lactic acid bacterium, wherein the YjaE protein is essentially inactive in the sense that the YjaE protein is functional inactive with respect to phage infection.

By the expression an "YjaE protein is functional inactive with respect to phage infection" is referred to an YjaE protein which differs from the YjaE protein sequence SEQ ID No. 2 and which is characterized by that a bacterium which carries a YjaE gene coding for said functional inactive YjaE protein has improved resistance to at least one bacteriophage, wherein the bacteriophage is selected from a suitable representative panel of different bacteriophages. A suitable representative panel of different bacteriophages preferably comprises different relevant phages representing prolate bacteriophage of the c2 species, small isometric phage of the 936 species, small isometric phages of the p335 species and large isometric phage of the 949 species. One particular representative panel of different bacteriophages is a panel which comprise prolate bacteriophages of the c2 species: bIL67, CHL92, MPC100, c2, 3, 24, 116, 122, 134, 180, 199, 227, 364, 670; small isometric bacteriophages of the 936 species: 234, 649; and small isometric bacteriophages of the P335 species: 228.

The term "improved resistance to a bacteriophage" denotes that the bacteria strain when tested in a plaque assay, such as the assay "determination of phage resistance by the agar overlay method" described below have an improved phage resistance to at least one phage expressed as the difference in pfu/ml (plaque forming unit per ml) obtainable with said at least one bacteriophage on the given strain, compared to the pfu/ml obtainable with the same bacteriophage on the parent strain. A strain with improved resistance to a bacteriophage preferably show a reduction of pfu/ml of a factor at least 50, such as at least 100, e.g. 500, preferably at least 1000, more preferably at least a factor 10000 or more.

Lactic Acid Bacterium

The term "lactic acid bacterium" denotes herein gram positive, micro-aerophilic or anaerobic bacteria, which ferment sugar with the production of acids including lactic acid as the predominantly produced acid, acetic acid, formic acid and propionic acid.

The industrially most useful lactic acid bacteria are found among *Lactococcus* species, *Streptococcus* species, *Lactobacillus* species, *Leuconostoc* species *Pediococcus* species and *Enterococcus* species. Also the strict anaerobes belonging to the genus *Bifidobacterum* are in generally included in the group of lactic acid bacteria.

As said above, members of the lactic acid bacteria *Lactococcus* subsp. are most devastated by bacteriophage infections.

Accordingly in a preferred embodiment the lactic acid bacterium is a *Lactococcus* sp., preferably a *Lactococcus lactis* species.

Preferred examples of *Lactococcus* subsp. are *Lactococcus lactis* subsp. *cremoris*, *Lactococcus lactis* subsp. *lactis* or *Lactococcus lactis* subsp. *lactis* biovar. *diacetylactis*.

As explained above *Lactococcus* subsp. contains a chromosomal gene (pip) for a membrane protein that serves as a receptor for the prolate bacteriophage c2 and other phages of the c2 species. In a preferred embodiment, the LAB as described herein also has the pip gene inactivated.

YjaE Protein and yjaE Gene

Based on the yjaE related sequence information known in art and disclosed herein it is relatively easy for the skilled person to identify if a gene in another type of LAB technically seen would be a yjaE gene.

For instance, the present inventors have sequences of the yjaE gene in 3 different strains of *Lactococcus* subsp. On amino acid level the three sequences were essentially identical to the sequence of the IL1430 strain (SEQ ID NO 2). For instance the sequence of the strain CAa120 has a Lys(K) at position 200 instead of the Glu(E) of IL1430. The rest of the sequence is identical to the one of IL1430.

Accordingly, in particular when the LAB is a *Lactococcus* subsp it is presently believed that different yjaE sequences in different strains are quite identical. However, without being limited to theory there is no reason to believe that future sequencing would not provide LAB from other genus that will comprise similar yjaE sequences.

As said above, the YjaE protein may be an YjaE protein that is expressed by an yjaE gene comprising a DNA sequence selected from the group consisting of:

(b) a DNA sequence that encodes a polypeptide, optionally having YjaE protein activity, that is at least 70% identical to the polypeptide sequence shown in positions 1-799 of SEQ ID NO 2 (IL1403 YjaE protein sequence).

The DNA sequence that encodes a polypeptide of (b), is preferably a DNA sequence that encodes a polypeptide that is at least 80%, such as at least 85%, identical to the polypeptide sequence shown in positions 1-799 of SEQ ID NO 2, more preferably at least 90% identical, even more preferably at least 93% identical and most preferably the DNA sequence that encodes a polypeptide of (b) is preferably a DNA sequence that encodes a polypeptide that is at least 96% or even 99% identical to the polypeptide sequence shown in positions 1-799 of SEQ ID NO 2.

The DNA sequence of (b) may e.g. be a non-natural variant of the DNA sequence of (a) that encodes a non-natural variant of the polypeptide. The skilled person knows how to make such variants e.g. by site-directed or random mutagenesis or by shuffling of similar genes.

Methods to Essentially Inactive the YjaE Protein

As discussed above, it is routine work for the skilled person to make a strain as described herein, where the YjaE protein is essentially inactive. Reference is made to working examples herein and the article of Kraus J. et al discussed in the Background section above.

Generally speaking a suitable routine method may be to introduce or replace via homologous recombination a suitable DNA fragment into the yjaE genomic gene sequence (e.g. by use of the publicly available pGhost vectors). If the introduced fragment for instance comprises a nonsense (stop) codon then the gene would be inactivated and the LAB will be a LAB with an inactive YjaE protein. Another suitable modification could be a frameshift mutation, a deletion, a mutation or an insertion. Alternatively, a suitable modification may be introduced a related region such as the promoter region.

As explained above a suitable modification of the yjaE gene may be many things such as a stop codon, an insertion that e.g. cause frame shift, a deletion, a mutation etc.

It is routine work for the skilled person to choose an adequate strategy to e.g. introduce a suitable modification of the yjaE gene in order not to get expression of an active YjaE protein.

Alternatively, one may randomly mutagenize (e.g. by UV radiation) and select for mutations wherein the YjaE protein is essentially inactive. Further one could select for relevant spontaneous mutations, wherein the YjaE protein is essentially inactive.

In a preferred embodiment the YjaE protein is inactive.

In a preferred embodiment the YjaE protein is inactive.

The YjaE protein may be rendered inactive due to mutations that e.g. introduce a frameshift or a stopcodon in the YjaE protein in particular if the mutation appear in the proximal half-part of the protein—see example 1 and 3. However, it appears that any mutation, including the 84 nucleotide in-frame deletion of position 2007-2090, which result in a protein that lacks at least one of the predicted transmembrane domains corresponding to amino acids 14-33, 625-642, 664-683, 691-710, 719-738 or 774-792 in the deduced protein sequence result in a inactive protein in the sense that the YjaE protein is functional inactive with respect to phage infection. Thus one embodiment of the present invention is a lactic acid bacterium, wherein the yjaE gene code for an YjaE protein that lacks at least one of the predicted transmembrane domains defined corresponding to amino acids 14-33, 625-642, 664-683, 691-710, 719-738 or 774-792 in the deduced protein sequence.

As discussed in example 4 it is possible to predict the intra- and extra-cellular positioning of the individual regions of the YjaE protein. It is contemplated that the intra- and extra-cellular positioning of the individual regions of the YjaE protein is important for its function during phage infection. In this connection the 84 nucleotide in-frame deletion of position 2007-2090 (aminoacids 670-697) appear particular interesting since this deletion result in a protein wherein the predicted intra- and extra-cellular positioning of the remaining parts of the protein is switched. Thus an alternative embodiment of the invention is a lactic acid bacterium, wherein the yjaE gene code for an YjaE protein wherein the predicted distribution of intra- and exracellular positioned domains of the YjaE protein have been changed relative to the predicted situation in strain IL1403.

Methods to Assay YjaE Protein Inactivation

As said above, a way to measure the inactivity of the YjaE protein is simply to analyze the bacterium for increased resistance to a suitable representative panel of different bacteriophages. Routinely this may be done by use of a standard plaque assay. See working example 1 for a description of a suitable plaque assay based on the agar overlay method. The plaque assay evaluates the phage resistance of a strain of interest (YjaE protein inactivated) as the difference in pfu/ml (plaque forming units per ml) obtainable with a given bacteriophage on the strain of interest, compared to the pfu/ml obtainable with the same bacteriophage on the parent strain (YjaE protein has natural wild-type activity).

Accordingly, a lactic acid bacterium as described herein may be characterized by that it has improved resistance to at least one bacteriophage, wherein the bacteriophage is selected from a suitable representative panel of different bacteriophages. See working examples herein for a preferred method to analyze resistance to bacteriophages.

A suitable representative panel of different bacteriophages should preferably comprise different relevant phages representing prolate bacteriophages of the c2 species, small isometric phage of the 936 species, small isometric phages of the p335 species and large isometric phage of the 949 species.

Suitable examples of prolate bacteriophages of the c2 species are bIL67, CHL92, MPC100, c2, 3, 24, 364, P001.

Suitable examples of small isometric phage of the 936 species are sk1, p2, jj50, 234, 649.

Suitable examples of small isometric phages of the p335 species are mm210b, 31, p335.

Suitable examples of large isometric phage of the 949 species are 949.

All the above listed phages are known from the scientific literature or may be obtained by request to Chr. Hansen A/S, Denmark.

Preferably, the lactic acid bacterium as described herein has improved resistance to a prolate bacteriophage of the c2 species and/or a small isometric phage of the 936 species.

An alternative way to measure the inactivity of the yjaE protein is to analyze the yjaE gene sequence to see if it comprises a suitable modification that cause e.g. an inactivation of the gene. As explained above a suitable modification may be many things such as a stop codon, an insertion that e.g. cause frame shift, a deletion, a mutation etc. It is routine for a skilled person (e.g. by sequencing the gene) to identify if the gene comprises such a suitable modification.

Accordingly, in a preferred embodiment the lactic acid bacterium as described herein comprises a suitable modification in the yjaE gene, wherein the modification results in that essentially no active YjaE protein is expressed.

More preferably, the modification results in that no active YjaE protein is expressed.

A further way to measure the inactivity of the yjaE protein is to analyze if active YjaE protein is present in the membrane of the bacterium. This may be done by a standard isolation method as described in working examples herein.

Accordingly, in a preferred embodiment the lactic acid bacterium as described herein does not comprise measurable amount of active YjaE protein in the membrane.

A Starter Culture Comprising a LAB as Described Herein

The lactic acid bacterium as described herein is useful as starter cultures in the production of food or feed products.

Typically, such a starter culture composition comprises the bacteria in a concentrated form including frozen, dried or freeze-dried concentrates typically having a concentration of viable cells which is in the range of $10^4$ to $10^{12}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g.

The composition may as further components contain cryoprotectants and/or conventional additives including nutrients such as yeast extracts, sugars and vitamins.

As it is normal in the production of lactic acid bacterial fermentation processes to apply mixed cultures of lactic acid bacteria, the composition will in certain embodiments comprise a multiplicity of strains either belonging to the same species or belonging to different species. A typical example of such a useful combination of lactic acid bacteria in a starter culture composition is a mixture of a *Leuconostoc* sp. and one or more *Lactococcus* subsp. such as *Lactococcus lactis* subsp. *lactis, Lactococcus lactis* subsp. *cremoris* or *Lactococcus lactis* subsp. *lactis* bio-var. *diacetylactis*.

A Method of Manufacturing a Food or Feed Product

As said above, an aspect of the invention relates to a method of manufacturing a food or feed product comprising adding a starter culture composition as described herein to a food or feed product starting material and keeping the thus inoculated starting material under conditions where the lactic acid bacterium is metabolically active.

Useful food product starting materials include any material which is conventionally subjected to a lactic acid bacterial fermentation step such as milk, vegetable materials, meat products, fruit juices, must, doughs and batters. The fermented products, which are obtained by the method, include as typical examples dairy products such as cheese including fresh cheese products, and buttermilk.

In further embodiments, the substrate material is a starting material for an animal feed such as silage e.g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

Yet another significant application of the lactic acid bacterium according to the present invention is the use of the bacterial cultures as so-called probiotics. By the term "probiotic" is in the present context understood a microbial culture which, when ingested in the form of viable cells by humans or animals, confers an improved health condition, e.g. by suppressing harmful microorganisms in the gastrointestinal tract, by enhancing the immune system or by contributing to the digestion of nutrients.

Identity of DNA Sequences:

The DNA sequence identity referred to herein is determined as the degree of identity between two sequences indicating a deviation of the first sequence from the second.

At the filing date of the present invention, the National Center for Biotechnology Information (NCBI) offered at its Internet site (http://www.ncbi.nlm.nih.gov/) the possibility of making a standard BLAST computer sequence homology search.

BLAST program is described in [Altschul et al (1997), "Gapped BLAST and PSI-BLAST: a new generation of protein database search programs", Nucleic Acids Res. 25:3389-3402].

In the present context, a preferred computer homology search program is a "Standard nucleotide-nucleotide BLAST [blastn]" search as specified, at the filing date of the present application, at the NCBI Internet site with setting filter: Low complexity; Expect: 10, Word Size: 11.

The reference sequence is introduced into the program and the program identifies fragments of published sequences together with the identity percentage to a corresponding fragment of the reference sequence.

Identity to Amino Acid Sequences

Similar to the nucleotide homology analysis, in the present context, a preferred computer homology search program is a "Standard protein-protein BLAST [blastp]" search as specified, at the filing date of the present application, at the NCBI Internet site with settings Composition-based statistics: yes, filter: Low complexity; Expect: 10, Word Size: 3, Matrix: BLOSUM 62, Gap Costs: Existence 11 Extension 1.

LEGEND

FIG. 1. Shows the predicted transmembrane regions and position of the deduced YjaE protein from CAa120 in the bacterial membrane. Numbers at arrow points refer to positions in the amino acid sequence (SEQ ID No. 2) and indicate the amino acids that border the membrane spanning regions.

EXAMPLES

Materials and Methods

Plaque Assay—Determination of Phage Resistance by the Agar Overlay Method

This method evaluates the phage resistance of a given mutant strain of *Lactococcus lactis* as the difference in pfu/ml (plaque forming unit per ml) obtainable with a given bacteriophage on the given strain, compared to the pfu/ml obtainable with the same bacteriophage on the parent strain. Plaques each origin from one bacteriophage and are seen as clear circular areas of no growth in a lawn of growing bacteria.

The desired strain was clean streaked on plates (M17+ needed additives). 5-10 single colonies were inoculated in liquid media and the $OD_{600}$ of the exponentially growing cultures was monitored. When the $OD_{600}$ of the culture was between 0.5 and 0.8, 100 μl of the culture was mixed with 100 μl of phages. This was repeated for phage-solutions with titers ranging from $10^{11}$ pfu/ml to 10 pfu/ml as measured on the parent strain. Cells and phages were mixed in a total of 3 ml top agar (M17, 10 mMCaCl$_2$, 0.75% agar), and poured onto plates (M17, 10 mM CaCl$_2$, 1.5% agar) and incubated for overnight at 30° C.

The plates were evaluated by counting the number of plaques formed. The pfu/ml of the used bacteriophage on the given strain was determined. The phage resistance of the given strain was determined as the ratio of the pfu/ml found for this strain and the parent strain.

Test to See If Active YjaE Protein is Present in the Membrane of the Bacterium

The cells are digested with lysozyme to separate the cell wall from the membranes, and the membranes are collected by standard procedures, e.g. differential centrifugation. The proteins are isolated from the membranes by solubilization using standard protein solubilization kits for membrane proteins, e.g. 2-D Sample Preparation for Membrane Proteins from Pierce Bio-technology (Rockford, Ill., USA) or ReadyPrep Protein Extraction Kit (Membrane I or II) from BioRad (Hercules, Calif., USA). Subsequently the solubilized proteins are subjected to two-dimensional gel electrophoresis in a pH range covering pH 7.5-9.5 (pl of the YjaE protein is 8.6-8.9) using standard procedures. The molecular weight of the YjaE protein (85 kDa) and the pI will determine its position in the two-dimensional gel, and an absent or altered (e.g. truncated) YjaE protein will be evident as compared to a parent strain. The identity of the YjaE protein of the parent strain can be verified by in-gel digestion and mass spectrometry.

REFERENCES

Valyasevi, R., Sandine, W. E., Geller, B. L., 1991. A membrane protein is required for bacterio-phage c2 infection of *Lactococcus lactis* subsp. *lactis* C2. J. Bact. 173(19), 6095-6100.

Silveira, M. G., Baumgärtner, M., Rombouts, F. M., Abee, T., 2004. Effect of adaptation to ethanol on cytoplasmic and membrane protein profiles of *Oenococcus oeni*. Appl. Environ. Microbiol. 70(5), 2748-2755.

Nouwens, A. S., Cordwell, S. J., Larsen, M. R., Molloy, M. P., Gillings, M., Willcox, M. D. P., Walsh, B. J., 2000. Complementing genomics with proteomics: the membrane subproteome of *Pseudomonas aeruginosa* PAO1. Electrophoresis 21, 3797-3809.

Molloy, M. P., Herbert, B. R., Slade, M. B., Rabilloud, T., Nouwens, A. S., Williams, K. L., Gooley, A. A., 2000. Proteomic analysis of the *Escherichia coli* outer membrane. Eur. J. Biochem. 267, 2871-2881.

Example 1

Inactivation of the yjaE Gene in *Lactococcus* Strains

Strains:
IL1403: Reference WO01/77334
CAa120:
Stuer-Lauridsen, B., Janzen, T., Schnabl, J., Johansen, E., 2003. Identification of the host determinant of two prolate-headed phages infecting *Lactococcus lactis*. Virology 309, 10-17.
Vectors:
pGhost vectors: For details see the articles
Maguin, E., Prévost, H., Gruss, A., 1996. Construction of food-grade mutants of lactic acid bacteria. Lait 76, 139-146.
Biswas, I., Gruss, A., Ehrlich, S. D., Maguin, E., 1993. High-efficiency gene inactivation and replacement system for Gram-positive bacteria. Journal of Bacteriology 175(11), 3628-3635.

Description of Inactivation Procedure:

A PCR fragment of 650 bp was generated covering the middle part of the yjaE gene from nt 703 to 1344. The template used was chromosomal DNA from *L. lactis* CAa120, and the fragment was cloned into the vector pGhost9. The PCR fragment contained a unique BsrGI site which, when filled out by the Klenow fragment and religated, was turned into a SnaBI site and caused a frameshift of one base. The construct was integrated into the chromosomal version of yjaE in CAa120 by homologous recombination, and the vector pGhost9 was subsequently successfully crossed out leaving behind the frameshift mutation. The mutation generated was verified by restriction analysis as well as by sequencing of a PCR fragment, and the mutant strain was named CAa120ΔyjaE. A similar construction was performed in *L. lactis* IL1403 and the mutant strain was named IL1403ΔyjaE. These strains were tested for resistance against the phages infecting the mother strains by plaque assays, and it was found that the constructed strains had become resistant to a number of the phages (i.e. the phages using the YjaE protein for infection). This inactivation of the yjaE gene is based on homologous recombination with a constructed fragment, which have been modified to produce a dysfunctional gene when replacing a normal fragment. The replacement was performed using pGhost9 as a vector but it could be done with any vector as the vector does not have to function in *L. lactis* for recombination to occur.

Results:

Following panel of phages was used in a plaque assay as described above:

Prolate bacteriophage of the c2 species: bIL67, CHL92, MPC100, c2, 3, 24, 116, 122, 134, 180, 199, 227, 364, 670.
Small isometric phage of the 936 species: 234, 649.
Small isometric phages of the p335 species: 228.
The results are shown in the table 1 below.

TABLE 1 showing infection (+) or no infection (−) by a number of phages in two *L. lactis* strains and their yjaE mutant variants.

|        | IL1403 | IL1403Δyja | CAa120 | CAa120Δyja |
|--------|--------|------------|--------|------------|
| 3      | +      | −          | +      | −          |
| 24     | +      | −          | +      | −          |
| 116    | +      | +          | −      | −          |
| 122    | +      | +          | −      | −          |
| 134    | +      | +          | −      | −          |
| 180    | +      | +          | −      | −          |
| 199    | +      | +          | −      | −          |
| 227    | +      | +          | −      | −          |
| 228    | +      | +          | −      | −          |
| 234    | −      | −          | +      | −          |
| 364    | −      | −          | +      | −          |
| 649    | −      | −          | +      | −          |
| 670    | −      | −          | +      | +          |
| CHL92  | +      | −          | +      | −          |
| bIL67  | +      | −          | −      | −          |
| MPC100 | +      | +          | −      | −          |
| c2     | +      | +          | −      | −          |

The results demonstrated that the strains with the yjaE gene inactivated have improved phage resistance towards both prolate bacteriophages of the c2 species and small isometric phage of the 936 species.

Further the strains were tested for viability, growth rate and acid production.

No measurable negative effects were seen as compared to the corresponding wild type strains.

Example 2

General Method for Generation of Spontaneous Phage Resistant Mutants

This method can be used to obtain spontaneous phage resistant mutants with mutations in the yjaE gene as confirmed by DNA sequencing.

The desired strain is inoculated by a scrape from a frozen stock in 10 ml liquid media M17 (Oxoid CM0817, Oxoid Ltd., Basingstoke, Hampshire, England)+needed additives. In the present case needed additives are 0.5% lactose for strain CAa120 and 34 and 0.5% glucose for strain IL1403 and Bu2-60. The $OD_{600}$ of the exponentially growing culture is monitored. When the $OD_{600}$ of the culture reaches between 0.5 and 0.8, 100 µl of the culture is mixed with phages at a multiplicity of infection (MOI) of 1-10 phages per cell. Cells and phages are mixed in a total of 3 ml top agar (M17, 10 mM $CaCl_2$, 0.75% agar) and poured onto plates (M17, 10 mM $CaCl_2$, 1.5% agar) and incubated at 30° C. for one or two days. Most cells are killed by the infecting phages, but spontaneous phage resistant mutant colonies will eventually appear. The frequency with which spontaneous phage resistant mutants appear, can vary from strain to strain.

The phage resistant mutants are picked up, clean-streaked on plates, and tested for phage resistance against the phage used in the generation procedure as well as against other phages infecting the parent strain by plaque assay as described elsewhere in this text.

The mutants are subsequently inoculated in liquid media and chromosomal DNA is extracted and used as basis for generating PCR fragments covering a desired gene, in the present case the yjaE gene. These PCR fragments are thereafter sequenced to determine in which way the DNA sequence of each mutant is different from that of the parent strain.

Example 3

Generation of Spontaneous Phage Resistant yjaE Mutants

Strains:
IL1403: *Lactococcus lactis*. Reference WO01/77334
CAa120: *Lactococcus lactis*. Reference Chr. Hansen Culture Collection. Stuer-Lauridsen, B., Janzen, T., Schnabl, J., Johansen, E., 2003. Identification of the host determinant of two prolate-headed phages infecting *Lactococcus lactis*. Virology 309:10-17.
Bu2-60: *Lactococcus lactis*. Wetzel, A., Neve, H., Geis, A., Teuber, M., 1986. Transfer of plasmid-mediated phage resistance in lactic acid Streptococci. Chem. Mikrobiol. Technol. Lebensm. 10:86-89.
Strain 34: *Lactococcus lactis*. Reference Chr. Hansen Culture Collection.
Strain CAa120 and 34 can be purchased from Chr. Hansen.
Description of Procedure:

The strains were taken through the procedure for generation of spontaneous phage resistant mutants as described under Materials and Methods, one strain and one phage in different combinations as follows: Strain 34 and p24, Bu2-60 and Φ3, Bu2-60 and Φ364, IL1403 and ΦbIL67, CAa120 and Φ24. PCR fragments covering the whole yjaE gene as well as approximately 150 nt up- and downstream from the start and stop codon of the gene were generated from each spontaneous mutant using chromosomal DNA as basis. These PCR fragments were sequenced and the sequence of each mutant was compared to that of the parent strain.
Results:

In total 21 spontaneous mutants were investigated by PCR and DNA sequencing. All mutant strains had mutations in the yjaE gene (see table 2 for details).

TABLE 2

| Spontaneous Mutations. All positions refer to DNA SEQ no.1. | |
|---|---|
| mutation | description |
| a at position 192 | a was missing in eight spontaneous mutants (three from 34, one from CAa120, one from IL1403, and three from Bu2-60), leading to a stop codon at position 224-226. |
| a at position 192 | One spontaneous mutant (from 34) had an extra a, leading to a stop codon at position 204-206. |
| a at position 291 | a was missing in two spontaneous mutants (from IL1403), leading to a stop codon at position 350-352. |
| c at position 419 | c was replaced by an a in one spontaneous mutant (from CAa120), leading to a stop codon at position 418-420. |
| c at position 766 | c was replaced by a t in two spontaneous mutants (from CAa120), leading to a stop codon at position 766-768. |
| c at position 865 | c was replaced by a t in one spontaneous mutant (from Bu2-60), leading to a stop codon at position 865-867. |
| a at position 998 | a was missing in two spontaneous mutants (one from IL1403 and one from CAa120), leading to a stop codon at position 1040-1042. |
| c at position 1869 | c was replaced by an a in one sponatneous mutant (from Bu2-60), leading to a stop codon at position 1867-1869. |
| position −111 to −16 | a deletion of 96 nt found in one spontaneous mutant (from Bu2-60), leading to deletion of the promoter upstream from the yjaE gene. |
| position 601 to 1987 | an in-frame deletion of 1386 nt was found in one spontaneous mutant (from CAa120) spanning the major part of the predicted big external loop and the first trans-membrane domain in the predicted membrane anchoring region of the deduced YjaE protein (corresponding to amino acids 201-663 in the deduced protein sequence). |
| position 2007 to 2090 | an in-frame deletion of 84 nt was found in one spontaneous mutant (from Bu2-60) in the predicted membrane anchoring region of the deduced YjaE protein (corresponding to amino acids 670-697 in the deduced protein sequence). |

The mutants were also tested for phage resistance against a number of phages as shown in the table 3 below.

All spontaneous phage resistant mutants showed improved phage resistance towards both prolate-headed bacteriophages of the c2 species and small isometric-headed phages of the 936 species. All spontaneous phage resistant mutants of each strain showed the same phage infection profile, therefore the columns showing spontaneous phage resistant mutants in the table are representative for all spontaneous mutants investigated in the present case.

TABLE 3 showing infection (+) or no infection (−) by a number of phages in different strains of Lactococcus lactis and their constructued (ΔyjaE) or spontaneous (spont) yjaE mutants see tab 2 for details on the spontaneous mutants.

| | IL 1403 | IL 1403 Δyja E | IL 1403 spont | CAa 120 | CAa 120 ΔyjaE | CAa 120 spont | Bu2-60 | Bu2-60 ΔyjaE | Bu2-60 spont | 34 | 34 spont |
|---|---|---|---|---|---|---|---|---|---|---|---|
| 3 | + | − | − | + | − | − | + | − | − | + | − |
| 24 | + | − | − | + | − | − | + | − | − | + | − |
| 116 | + | + | + | − | − | − | + | − | − | − | − |
| 122 | + | + | + | − | − | − | + | + | − | − | − |
| 134 | + | + | + | − | − | − | + | + | − | − | − |
| 180 | + | + | + | − | − | − | − | − | − | − | − |
| 199 | + | + | + | − | − | − | + | + | − | − | − |
| 227 | + | + | + | − | − | − | + | + | − | − | − |
| 228 | + | + | + | − | − | − | − | − | − | − | − |
| 234[c] | − | − | − | + | − | − | + | + | − | + | − |
| 364 | − | − | − | + | − | − | − | − | − | + | − |
| 649[c] | − | − | − | + | − | − | − | − | − | + | − |
| 670 | − | − | − | + | + | + | − | − | − | + | + |
| CHL92 | + | − | − | + | − | − | + | + | − | − | − |
| biL67 | + | − | − | − | − | − | − | − | − | − | − |
| MPC100 | + | + | + | − | − | − | − | − | − | − | − |
| c2 | + | + | + | − | − | − | − | − | − | − | − |

TABLE 3-continued

Prolate bacteriophages of the c2 species: biL67, CHL92, MPC100, c2, 3, 24, 116, 122, 134, 180, 199, 227, 364, 670.
Small isometric bacteriophages of the 936 species: 234, 649.
Small isometric bacteriophages of the P335 species: 228.

Example 4

Prediction of Transmembrane Regions in the Deduced YjaE Protein

Several public websites offer the service of predicting transmembrane regions of proteins from the amino acid sequence, e.g. the Swiss Embnet at www.ch.embnet.org and the Prediction Servers of Center for Biological Sequence Analysis at DTU at www.genome.cbs.dtu.dk/services/. The amino acid sequence deduced from the yjaE gene sequence from CAa120 was entered into the TMPRED of Swiss Embnet and gave the predicted transmembrane regions and position in the bacterial membrane for the YjaE protein as shown in FIG. 1. A prediction from the CBS Server at DTU gave similar results.

The invention claimed is:

1. A lactic acid bacterium wherein an YjaE protein, expressed by an yjaE gene, is inactive, wherein said inactive YjaE protein is functionally inactive with respect to phage infection, and wherein the YjaE protein is expressed by a yjaE gene comprising a DNA sequence selected from the group consisting of:
   (a) the DNA sequence of SEQ ID NO 1 (IL1403 yjaE DNA coding sequence); and
   (b) a DNA sequence that encodes a polypeptide, having YjaE protein activity, that is at least 70% identical to the polypeptide sequence of SEQ ID NO 2 (IL1403 YjaE protein sequence); and wherein the YjaE protein is inactive due to a modification introduced into the yjaE gene.

2. The lactic acid bacterium of claim 1, wherein said bacterium has an improved resistance to a bacteriophage.

3. The lactic acid bacterium of claim 1, wherein the lactic acid bacterium is a *Lactococcus* sp.

4. The lactic acid bacterium of claim 1, wherein the DNA sequence that encodes a polypeptide of (b), is a DNA sequence that encodes a polypeptide that is at least 90% identical to the polypeptide sequence of SEQ ID NO 2.

5. The lactic acid bacterium of claim 1, wherein the yjaE gene codes for an YjaE protein that lacks at least one of the predicted transmembrane domains.

6. The lactic acid bacterium of claim 1, wherein said modification is selected from the group consisting of a stop codon, an insertion, a deletion, and a mutation.

7. The lactic acid bacterium of claim 1, wherein the lactic acid bacterium has improved resistance to at least one bacteriophage, wherein the bacteriophage is selected from a representative panel of different bacteriophages.

8. A starter culture composition comprising the lactic acid bacterium of claim 1.

9. A method of manufacturing a food or feed product comprising adding a starter culture composition according to claim 8 to a food or feed product starting material and keeping the thus inoculated starting material under conditions where the lactic acid bacterium is metabolically active.

10. A method for making a lactic acid bacterium of claim 1, wherein the YjaE protein, expressed by the yjaE gene, is inactive, wherein said inactive YjaE protein is functionally inactive with respect to phage infection, comprising making a suitable modification of the yjaE gene in order not to get expression of an active YjaE protein, wherein the yjaE gene comprises a DNA sequence selected from the group consisting of:
   (a) the DNA sequence of SEQ ID NO 1 (IL1403 yjaE DNA coding sequence);
   (b) a DNA sequence that encodes a polypeptide, having YjaE protein activity, that is at least 80% identical to the polypeptide sequence of SEQ ID NO 2 (IL1403 YjaE protein sequence).

11. The lactic acid bacterium of claim 2, wherein said bacterium shows a reduction of pfu/ml of a factor of at least 50.

12. The lactic acid bacterium of claim 11, wherein said bacterium shows a reduction of pfu/ml of a factor, of at least 100.

13. The lactic acid bacterium of claim 12, wherein said bacterium shows a reduction of pfu/ml of a factor of at least 500.

14. The lactic acid bacterium of claim 13, wherein said bacterium shows a reduction of pfu/ml of a factor of at least 1000.

15. The lactic acid bacterium of claim 14, wherein said bacterium shows a reduction of pfu/ml of a factor of at least 10000.

16. The lactic acid bacterium of claim 3 wherein the lactic acid bacterium is a *Lactococcus* sp, selected from the group consisting of *Lactococcus lactis* subsp, *cremoris*, *Lactococcus lactis* subsp, *lactis* and *Lactococcus lactis* subsp, *lactis* biovar, *diacetylactis*.

17. The lactic acid bacterium of claim 4 wherein the DNA sequence that encodes a polypeptide of (b), is a DNA sequence that encodes a polypeptide that is at least 96% identical to the polypeptide sequence of SEQ ID NO:2.

18. The lactic acid bacterium of claim 7 wherein said modification is an insertion that causes a frame shift.

19. The lactic acid bacterium of claim 7, wherein said representative panel of different bacteriophages comprises different relevant phages representing prolate bacteriophage of the c2 species, small isometric phage of the 936 species, small isometric phages of the p335 species and large isometric phage of the 949 species.

20. The starter culture composition of claim 8 wherein the starter culture composition has a concentration of viable cells which is in the range of $10^4$ to $10^{12}$ cfu per gram of the composition.

* * * * *